United States Patent [19]
Yeske et al.

[11] Patent Number: 5,910,579
[45] Date of Patent: Jun. 8, 1999

[54] PROCESSES FOR THE PREPARATION OF αGAL(1->4)βGAL (1->4) GLC-OR

[75] Inventors: Robert E. Yeske, St. Albert; Robert A. Verhagen, Calgary; Joaquin Roberto Mendez, Edmonton, all of Canada

[73] Assignee: Synsorb Biotech Inc., Alberta, Canada

[21] Appl. No.: 08/941,030

[22] Filed: Sep. 30, 1997

Related U.S. Application Data

[63] Continuation-in-part of application No. 08/781,327, Jan. 10, 1997, abandoned.
[51] Int. Cl.$^6$ .............. C07H 3/06; C07H 1/00; A61K 31/715
[52] U.S. Cl. ............ 536/18.5; 514/61; 536/4.1; 536/18.6; 536/120; 536/123; 536/123.1
[58] Field of Search ............... 536/4.1, 18.5, 536/18.6, 120, 123, 123.1; 514/61

[56] References Cited

U.S. PATENT DOCUMENTS

| | | | |
|---|---|---|---|
| 5,079,353 | 1/1992 | Ratcliffe et al. | 536/53 |
| 5,620,858 | 4/1997 | Armstrong et al. | 435/7.8 |

OTHER PUBLICATIONS

*Biological Functions of Gangliosides: Proceedings of Nobel Symposium 83*, Ed. Svennerholm et al., p. XIV, 1994.
*Preparative Carbohydrate Chemistry*, Ed. Stephen Hanessian, Marcel Dekker Inc., pp. 333–334, 1997.
Barresi and Hindsgaul,. "Glycosylation Methods in Oligosacc–haride Synthesis" from *Modern Synthetic Methods*, Ed. Ernst and Leumann, VCH Publ., pp. 281–330, 1995.
QUI et al., *Liebigs. Ann. Chem.*, pp. 217–224. "Synthesis of Globotriasylceramide (Gb$_3$) and Isoglobotriaosylceramide (isoGb$_3$)", 1992.
Hashimoto et al., *Tetrahedron Letters*, vol. 38(52): 8969–8972, 1997.
Koike et al., "Total Synthesis of Globotriaosyl–E and Z–Cera–mides and Isoglobotriaosyl–E–Ceramides", *Carbohydrate Res.*, vol. 163:189–208, 1987.
Nicolaov et al. "Total Synthesis of Globotriaosylceramide (Gb$_3$) and lysoglobotriaosylceramide (lyso Gb$_3$)"*Carbohydrate Res.*, vol. 202: 177–191, 1990.

Ekborg, et al., "Synthesis of Three Disaccharides for the Preparation of Immunogens Bearing Immunodeterminants Known to Occur on Glycoproteins", *Carbohydr. Res.*, 110:55–67 (1982).
Dahmen, et al., 2–Bromoethyl Glycosides:Applications in the Synthesis of Spacer–Arm Glycosides *Carbohydr. Res.*, 118:292–301. (1983).
Rana, et al., "Synthesis of Phenyl 2–Acetamido–2–Deoxy–3–O–α–L–Fucopyranosyl–β–D–Glucopyranoside and Related Compounds", *Carbohydr. Res.*, 91:149–157 (1981).
Amvam–Zollo, et al., "*Streptococcus pneumoniae*Type XIV Polysaccharide: Synthesis of a Repeating Branched Tet-rasaccharide with Dioxa–Type Spacer–Arms" *Carbohydr. Res.*, 150:199–212 (1986).
Paulsen, et al., "Synthese Von Oligosaccharid–Determi-nanten Mit Amid–Spacer Vom Typ Des T–Antigens*", *Carbohydr. Res.*, 104:195–219 (1984).
Chernyak, et al., "A New Type of Carbohydrate–Containing Synthetic Antigen: Synthesis of Carbohydrate–Containing Polyacrylamide Copolymers Having the Specificity of O:3 and O:4 Factors of Salmonella", *Carbohydr. Res.*, 128:269–282 (1984).
Fernandez–Santana, et al., "Glycosides of Monoallyl Diethylene Glycol. A new Type of Spacer Group for Synthetic Oligosaccharides", *J. Carbohydr. Chem.*, 8:531–537 (1989).
Lee, et al., "Synthesis of 3–(2–aminoethylthio)propyl Glycosides", *Carbohydr. Res.*, 37:193 et seq., (1974).
Lemieux, et al., "The Properties of a "Synthetic" Antigen Related to the Human Blood–Group Lewis a", *J. Am. Chem. Soc.*, 97:4076–4083 (1975).
Pinto, et al., "Preparation of Glycoconjugates for Use as Artificial Antigens: A Simplified Procedure", *Carbohydr. Chem.*, 124:313–318 (1983).

*Primary Examiner*—John Kight
*Assistant Examiner*—Howard C. Lee
*Attorney, Agent, or Firm*—Burns, Doane, Swecker & Mathis L.L.P.

[57] ABSTRACT

Disclosed are novel synthetic processes for the preparation of the trisaccharide αGal(1→4)βGal(1→4)Glc-OR compounds.

10 Claims, 4 Drawing Sheets

PROCESSES FOR THE PREPARATION OF αGAL(1->4)βGAL (1->4) GLC-OR

CROSS-REFERENCE TO RELATED APPLICATIONS

This application is a continuation-in-part of U.S. patent application Ser. No. 08/781,327 filed Jan. 10, 1997, now abandoned which is incorporated by reference herein in its entirety.

BACKGROUND OF THE INVENTION

1. Field of the Invention

This invention is directed to novel synthetic processes for the preparation of the trisaccharide glycoside αGal(1→4)βGal(1→4)Glc-OR. Specifically, this invention is directed to a multi-step synthesis of this trisaccharide aglycon wherein the attachment of the aglycon is conducted after formation of the blocked βGal(1→4)Glc disaccharide which, surprisingly, significantly enhances the overall synthetic yield of the process.

2. References

The following publications, patents and patent applications are cited in this application as superscript numbers:

[1] Armstrong, et al., U.S. patent application Ser. No. 08/126,645 (allowed) for "Diagnosis and Treatment of Bacterial Dysentery", filed Sep. 27, 1993.

[2] Ratcliffe, et al., U.S. Pat. No. 5,079,353, for "SIALIC ACID GLYCOSIDES, ANTIGENS, IMMUNOADSORBENTS, AND METHODS FOR THEIR PREPARATION" issued Jan. 7, 1992.

[3] Ekborg, et al., "Synthesis of Three Disaccharides for the Preparation of Immunogens Bearing Immunodeterminants Known to Occur on Glycoproteins", Carbohydr. Res., 110:55–67 (1982).

[4] Dahmen, et al., "2-Bromoethyl Glycosides: Applications in the Synthesis of Spacer-Arm Glycosides Carbohydr. Res.", 118:292–301. (1983)

[5] Rana, et al., "Synthesis of Phenyl 2-Acetamido-2-Deoxy-3-O-α-L-Fucopyranosyl-β-D-Glucopyranoside and Related Compounds", Carbohydr. Res., 91:149–157 (1981).

[6] Amvam-Zollo, et al., "Type XIV Polysaccharide: Synthesis of a Repeating Branched Tetrasaccharide with Dioxa-Type Spacer-Arms" Carbohydr. Res., 150:199–212 (1986).

[7] Paulsen, et al., "Synthese Von Oligosaccharid-Determinanten Mit Amid-Spacer Vom Typ Des T-Antigens*", Carbohydr. Res., 104:195–219 (1984).

[8] Chernyak, et al., "New Type of Carbohydrate-Containing Synthetic Antigen: Synthesis of Carbohydrate-Containing Polyacrylamide Copolymers Having the Specificity of 0:3 and 0:4 Factors of Salmonella", Carbohydr. Res., 128:269–282 (1984).

[9] Fernadez-Santana, et al., "Glycosides of Monoallyl Diethylene Glycol. A new Type of Spacer Group for Synthetic Oligosaccharides", J. Carbohydr. Chem., 8:531–537 (1989).

[10] Lee, et al., "Synthesis of 3-(2-aminoethylthio)propyl Glycosides", Carbohydr. Res., 37:193 et seq., (1974).

[11] Lemieux, et al., "Properties of a "Synthetic" Antigen Related to the Human Blood-Group Lewis a", J. Am. Chem. Soc., 97:4076–4083 (1975)

[12] Pinto, et al., "Preparation of Glycoconjugates for Use as Artificial Antigens: A Simplified Procedure", Carbohydr. Chem., 124:313–318 (1983)

[13] Rafter, et al., U.S. patent application Ser. No. 08/669,004, for "Treatment of Bacterial Dysentery" filed Jun. 21, 1996

All of the above publications, patent applications and patents are herein incorporated by reference in their entirety to the same extent as if each individual publication, patent or patent application was specifically and individually indicated to be incorporated by reference in its entirety.

3. State of the Art

Trisaccharide glycosides, such as the αGal(1→4)βGal(1→4)Glc-OR trisaccharide, have been disclosed by Armstrong, et al.[1] as binding to Shiga Like Toxins (SLTs) expressed by pathogenic E. coli which can populate the intestinal tract of humans and cause diarrhea. In extreme cases, the pathology of this disease mediated by such toxins progresses to kidney involvement in the form of hemolytic uremic syndrome (HUS) which has a relatively high mortality rate. Accordingly, pharmaceutical compositions comprising such trisaccharides have been proposed for treatment of diarrhea mediated by SLTs.[13]

Notwithstanding the beneficial properties of such trisaccharides, current synthetic processes for these compounds involve a multi-step process with overall low yields. This, in turn, has hampered the commercial development of these compounds.

Specifically, the complete chemical synthesis of oligosaccharide glycosides is a difficult task involving the generation of differentially protected or blocked hydroxyl groups on at least some of the hydroxyl groups of each of the saccharide units so as to provide a means to selectively remove one or more of the blocking groups thereby permitting the necessary reactions to be conducted on the unblocked hydroxyl group(s) as required to generate the desired compound[2]. Additionally, the numerous reaction procedures required in blocking and deblocking different hydroxyl groups necessitate a multi-step chemical synthetic procedure and the generation of crystalline intermediates during the synthetic procedure is certainly desirable in providing a facile means to purify the intermediates other than by chromatography or other equivalent means. In this regard, chromatography on intermediates and products achieved by large scale synthesis of trisaccharide glycosides is recognized as a time consuming process which can require the use of expensive equipment and is generally disadvantageous to an efficient large scale overall synthesis of the desired trisaccharide glycoside.

Contrarily, the use of glycosyltransferases to effect overall synthesis of the desired trisaccharide glycoside can be hindered by the lack of ready availability of the required glycosyltransferase, the difficulty in effecting large scale enzymatic reactions, the difficulty in coupling the desired saccharide to the nucleotide base required for coupling, etc.

SUMMARY OF THE INVENTION

This invention is directed to novel processes for the overall chemical synthesis of αGal(1→4)βGal(1→4)Glc-OR[1] which processes involve the derivation of a readily available lactose disaccharide derivative. Specifically and contrary to prior art processes, the processes of this invention defer attachment of the aglycon substituent (i.e., the R[1] group) until after lactose disaccharide structure has been fully protected. Surprisingly, by so deferring such an attachment, the overall yields of this trisaccharide are significantly improved.

In addition to the above, some of the intermediates generated by deferred attachment of this aglycon substituent are readily crystalline which further facilitates the overall synthetic process by eliminating chromatography steps which correspondingly facilitates the synthesis and can enhance the overall yield.

Additionally, in the herein described processes, the synthesis of the trisaccharide glycoside is completed in such a fashion that the number of manipulations at the disaccharide and trisaccharide levels is kept to a minimum and yield is improved. For example, notwithstanding the numerous reaction procedures involved in converting disaccharide 3 in FIG. 1 to αGal(1→4)βGal(1→4)Glc-O(CH$_2$)$_8$COOCH$_3$ (compound 12 in FIG. 4), the yield achieved by the processes of this invention for this conversion is approximately 14 percent.

Accordingly, in one of its process aspects, this invention is directed to a process for the synthesis of αGal(1→4)βGal (1→4)Glc-OR$^1$ compounds which process comprises:

(a) contacting β-thio-R lactoside with at least a stoichiometric amount of an α,α-dialkoxytoluene wherein the toluene group is optionally substituted on the phenyl ring with 1 to 3 substituents independently selected from alkyl, alkoxy, cyano, halo, nitro, and trihalomethyl under conditions to provide for β-thio-R 4'-6'-di-O-benzylidene lactoside wherein R is selected from the group consisting of alkaryl, alkyl and aryl optionally substituted with 1 to 2 substituents selected from halo, alkyl, and alkoxy and further wherein the benzylidene group of the resulting β-thio-R 4'-6'-di-O-benzylidene lactoside is optionally substituted on the phenyl ring with 1 to 3 substituents selected from alkyl, alkoxy, cyano, halo, nitro, and trihalomethyl;

(b) benzoylating the compound produced in (a) above with at least 5 equivalents of benzoyl halide under conditions to provide for β-thio-R 4',6'-di-O-benzylidene-2,2',3, 3',6-penta-O-benzoyl-lactoside;

(c) contacting the compound produced in (b) above with a reactive halide compound under conditions to provide for either the α-chloro 4',6'-di-O-benzylidene-2,2',3,3',6-penta-O-benzoyl-lactoside or the α-bromo 4',6'-di-O-benzylidene-2,2',3,3',6-penta-O-benzoyl-lactoside;

(d) contacting the compound produced in (c) above with a compound of the formula HOR$^1$ where R$^1$ is an aglycon of at least one carbon atom under conditions to provide for β-aglycon 4',6'-di-O-benzylidene-2,2',3,3',6-penta-O-benzoyl-lactoside;

(e) contacting the compound produced in (d) above with a reducing agent under conditions which provide for β-aglycon 2,2',3,3',6-penta-O-benzoyl-6'-O-benzyl-lactoside wherein the benzyl group is optionally substituted on the phenyl ring with 1 to 3 substituents selected from alkyl, alkoxy, cyano, halo, nitro, and trihalomethyl;

(f) contacting the compound produced in (e) above with β-thiobenzyl 2,3,4,6-tetra-O-benzyl-D-galactose under conditions to provide for aglycon (2'',3'',4'',6''-tetra-O-benzyl-α-D-galactopyranosyl)-(1→4)-O-(2',3'-di-O-benzoyl-6'-O-benzyl-β-D-galactopyranosyl)-(1→4)-O-(2,3,6-tri-O-benzoyl-β-D-glucopyranoside); and (g) removing the benzyl and benzoyl protecting groups in the compound produced in (f) above under conditions to provide for α-D-galactopyranosyl-(1→4)-O-β-D-galactopyranosyl-(1→4)-O-β-D-glucopyranoside which can also be referred to as αGal(1–4)βGal(1→4)Glc-OR$^1$ where R$^1$ is an aglycon of at least 1 carbon atom.

Preferably, in the process described above, β-thio-R lactoside is prepared by:

(a) contacting at least a stoichiometric amount of RSH with peracetyl lactose wherein R is selected from the group consisting of alkyl, aryl, alkaryl and aryl substituted with 1 to 3 substituents selected from halo, alkyl and alkoxy under conditions which form the β-thio-R 2,2',3,3',4,6,6'-hepta-O-acetyllactoside; and (b) deacetylating the product produced in (a) above under conditions to provide for β-thio-R lactoside.

A particular embodiment of the present invention is directed to a process for the synthesis of αGal(1→4)βGal (1→4)Glc-O(CH$_2$)$_8$COOCH$_3$ which process comprises:

(a) contacting β-thiobenzyl lactoside with at least a stoichiometric amount of a α,α-dimethoxytoluene under conditions to form β-thiobenzyl 4'-6'-di-O-benzylidene lactoside;

(b) benzoylating the compound produced in (a) above with at least 5 equivalents of benzoyl halide under conditions to provide for β-thiobenzyl 4',6'-di-O-benzylidene-2, 2',3,3',6-penta-O-benzoyl-lactoside;

(c) contacting the compound produced in (b) above with X$_2$ wherein X is selected from the group consisting of Br and Cl under conditions to provide for either the α-bromo 4',6'-di-O-benzylidene-2,2',3,3',6-penta-O-benzoyl-lactoside or the α-chloro 4',6'-di-O-benzylidene-2,2',3,3',6-penta-O-benzoyl-lactoside;

(d) contacting the compound produced in (c) above with a compound of the formula HO(CH$_2$)$_8$COOCH$_3$ under conditions to provide for 8-methoxycarbonyloctyl 4',6'-di-O-benzylidene-2,2',3,3',6-penta-O-benzoyl lactoside;

(e) treating the compound produced in (d) above with a reducing agent under conditions to provide for 8-methoxycarbonyloctyl 2,2',3,3',6-penta-O-benzoyl-6'-O-benzyl-lactoside;

(f) contacting the compound produced in (e) above with β-thiobenzyl 2,3,4,6-tetra-O-benzyl-D-galactose to provide for 8-methoxycarbonyloctyl (2'',3'',4'',6''-tetra-O-benzyl-α-D-galactopyranosyl)-(1→4)-O-(2',3'-di-O-benzoyl-6'-O-benzyl-β-D-galactopyranosyl)-(1→4)-O-(2,3,6-tri-O-benzoyl-β-D-glucopyranoside); and (g) removing each of the benzyl and benzoyl protecting groups in the compound produced in (f) above under conditions to provide for 8-methoxycarbonyloctyl-α-D-galactopyranosyl-(1→4)-O-β-D-galactopyranosyl-(1→4)-O-β-D-glucopyranoside which can also be referred to as αGal(1→4)βGal(1→4)Glc-O(CH$_2$)$_8$COOCH$_3$.

DETAILED DESCRIPTION OF THE INVENTION

Figure 1:
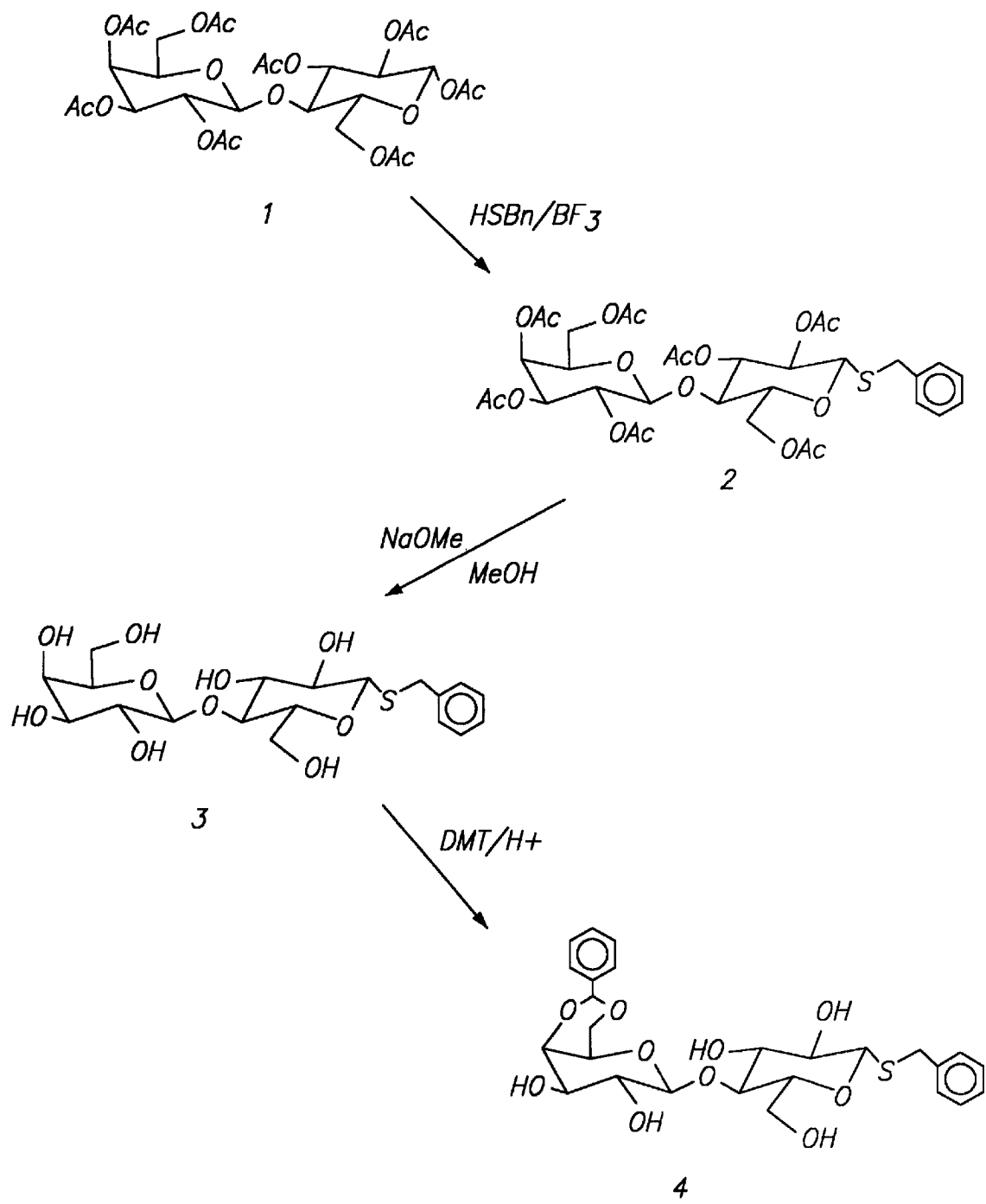
FIGS. 1–4 illustrate the synthetic procedure for the preferred 8-methoxycarbonyloctyl α-D-galactopyranosyl-(1→4)-O-β-D-galactopyranosyl-(1→4)-O-β-D-glucopyranoside starting with peracetyl lactoside.

This invention is directed to processes for the preparation of the trisaccharide αGal(1→4)βGal(1→4)Glc-OR.

Prior to discussing this invention in further detail, the following terms will first be defined:

The term "lactose" refers to the disaccharide βGal(1→4) Glc which can be represented by the formula:

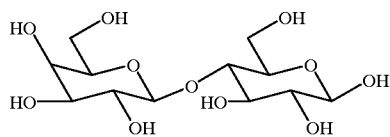

The term "lactoside" refers to the disaccharide βGal (1→4)Glc-YR where Y is oxygen or sulfur and R is an aglycon of at least one carbon atom. Thus, the term "β-thio-R lactoside" refers to the disaccharide βGal(1→4) Glc-SR wherein the —SR group has a β configuration. When R is an alkaryl group such as benzyl the lactoside is referred to as β-thioalkaryl lactoside or, when R is benzyl, as the β-thiobenzyl lactoside.

The term "aglycon of at least one carbon atom" refers to non-saccharide containing residues having at least one carbon atom, preferably from 1 to 20 carbon atoms and more preferably from 1 to 10 carbon atoms. Even more preferably, the aglycon is selected from the group consisting of -(A)-Z wherein A represents a bond, an alkylene group of from 2 to 10 carbon atoms, and a moiety of the form -(WG)$_n$- wherein n is an integer equal to 1 to 5; W is a straight or branched chain alkylene group of from 2 to 10 carbon atoms optionally substituted with 1 to 3 substituents selected from the group consisting of aryl of 6 to 10 carbon atoms and aryl of from 6 to 10 carbon atoms substituted with from 1 to 3 substituents selected from the group consisting of amino, hydroxyl, halo, alkyl of from 1 to 4 carbon atoms and alkoxy of from 1 to 4 carbon atoms; G is selected from the group consisting of a bond, O, S and NH; and Z is selected from the group consisting of hydrogen, methyl, phenyl, nitrophenyl and, when G is not oxygen, sulphur or nitrogen and when A is not a bond, then Z is also selected from the group consisting of —OH, —SH, —NH$_2$, —NHR$^2$, —N(R$^2$)$_2$, —C(O)OH, —C(O)OR$^2$, —C(O)NH—NH$_2$, —C(O)NH$_2$, —C(O)NHR$^2$, —C(O)N(R$^2$)$_2$, and —OR$^3$ wherein each R$^2$ is independently alkyl of from 1 to 4 carbon atoms and R$^3$ is an alkenyl group of from 3 to 10 carbon atoms.

Preferably, the aglycon contains a functional group or can be derivatized to contain a functional group which allows the aglycon to covalently bond to a solid support thereby providing for a compatible linker arm between the oligosaccharide and the solid support.

Numerous aglycons are known in the art. For example, an aglycon comprising a p-nitrophenyl group (i.e., —OR=—OC$_6$H$_4$(p)NO$_2$) has been disclosed by Ekborg, et al.[3] At the appropriate time during synthesis, the nitro group is reduced to an amino group which can be protected as N-trifluoroacetamido. When desired, the trifluoroacetamido group is removed thereby unmasking the amino group which can be used for coupling to a solid support.

An aglycon containing sulfur is disclosed by Dahmen, et al.[4] Specifically, the aglycon is derived from a 2-bromoethyl group which, in a substitution reaction with thionucleophiles, has been shown to lead to aglycons possessing a variety of terminal functional groups such as —OCH$_2$CH$_2$SCH$_2$CO$_2$CH$_3$ and —OCH$_2$CH$_2$SC$_6$H$_4$-p-NH$_2$ both of which can be used to couple this aglycon to a solid support.

Rana, et al.[5] discloses a 6-trifluoroacetamidohexyl aglycon [—O(CH$_2$)$_6$NHCOCF$_3$] in which the trifluoroacetamido protecting group can be removed unmasking the primary amino group which, again, can be used to couple this aglycon to a solid support.

Other exemplifications of known aglycons include the 7-methoxycarbonyl-3,6-dioxaheptyl aglycon[6] (—OCH$_2$CH$_2$)$_2$OCH$_2$CO$_2$CH$_3$; the 2-(4-methoxycarbonylbutancarboxamido)ethyl[7] [—OCH$_2$CH$_2$NHC(O)(CH$_2$)$_4$CO$_2$CH$_3$]; and the allyl aglycon[8] (—OCH$_2$CH=CH$_2$) which, by radical co-polymerization with an appropriate monomer, leads to co-polymers; other allyl linking aglycons[9] are known [e.g., —O(CH$_2$CH$_2$O)$_2$CH$_2$CH=CH$_2$]. Additionally, allyl linking arms can be derivatized in the presence of 2-aminoethanethiol[10] to provide for the aglycon of the formula —OCH$_2$CH$_2$CH$_2$SCH$_2$CH$_2$NH$_2$. As before, such aglycons permit covalent linkage to a solid support containing reactive groups complementary to the groups on the aglycon. That is to say that a complementary reactive group on the solid support is one which will selectively react with a reactive functionality on the aglycon to provide for covalent linkage therebetween.

Additionally, as shown by Ratcliffe, et al.[2], the aglycon R$^1$ group can be an additional saccharide-OR$^4$ or an oligosaccharide-OR$^4$ at the reducing sugar terminus (where R$^4$ is an aglycon as defined above).

Preferably, the aglycon moiety is a hydrophobic group and most preferably, the aglycon moiety is a hydrophobic group selected from the group consisting of —(CH$_2$)$_8$COOCH$_3$, —(CH$_2$)$_5$OCH$_2$CH=CH$_2$ and —(CH$_2$)$_8$CH$_2$OH.

The term "compatible linker arm" refers to a moiety which serves to space the oligosaccharide structure from the solid support and which is bifunctional wherein one functional group is capable of binding to a reciprocal functional group of the support and the other functional group is capable of binding to a reciprocal functional group of the oligosaccharide structure. Compatible linker arms preferred in the present invention are non-peptidyl spacer arms.

In a preferred embodiment, the aglycon attached to the oligosaccharide comprises functionality or can be derivatized to contain functionality which permits attachment of the aglycon to the solid support. For example, allyl groups, nitro groups, carboxyl esters can be derivatized via conventional synthetic methods to permit covalent linkage to a compatible functional group on the surface of a solid support. Epoxides, amines, hydrazines, and similar groups on the aglycon can be reacted directly with a compatible functional group on the surface of a solid support to effect covalent linkage.

The term "solid support" refers to an inert, solid material to which the oligosaccharide sequences may be bound via a compatible linker arm. Where use is in vivo, the solid support will be biocompatible and preferably non-immunogenic.

For purpose of this application, all sugars are referenced using conventional three letter nomenclature. All sugars are assumed to be in the D-form unless otherwise noted, except for fucose, which is in the L-form. Further all sugars are in the pyranose form.

The term "pharmaceutically acceptable salts" include any and all pharmaceutically acceptable addition salts of αGal (1→3)βGal(1→4)Glc-OR compounds derived from a variety of organic and inorganic counter ions well known in the art and include, by way of example only, sodium, potassium, calcium, magnesium, ammonium, tetraalkylammonium, and the like.

The term "removable blocking group" refers to any group which when bound to one or more hydroxyl groups of either or both galactose units or the glucose unit, used to prepare the αGal(1→4)βGal(1→4)Glc-OR compounds described herein prevents reactions from occurring at these hydroxyl groups and which protecting groups can be removed by conventional chemical and/or enzymatic procedures to reestablish the hydroxyl group without otherwise unintentionally altering the structure of the compound. The particular removable blocking group employed is not critical and preferred removable hydroxyl blocking groups include conventional substituents such as benzyl, benzoyl, acetyl, chloroacetyl, benzylidene, t-butylbiphenylsilyl and any other group that can be introduced onto a hydroxyl functionality and later selectively removed by conventional methods in mild conditions compatible with the nature of the product.

As used herein, "alkyl" refers to alkyl groups preferably having from 1 to 6 carbon atoms and more preferably 1 to 4 carbon atoms. This term is exemplified by groups such as methyl, ethyl, n-propyl, iso-propyl, n-butyl, tert-butyl, sec-butyl, n-pentyl, n-hexyl, 1,2-dimethylbutyl, and the like.

"Alkoxy" refers to the group "alkyl-O-" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Aryl" refers to an unsaturated aromatic carbocyclic group of from 6 to 10 carbon atoms having a single ring (e.g., phenyl) or multiple condensed rings (e.g., naphthyl).

"Alkaryl" refers to alkyl groups containing 1 to 2 aryl substituents thereon. Such groups preferably comprise from 7 to 18 carbon atoms and are represented by benzyl, —CH$_2$CH$_2$-φ, —CH(φ)$_2$ and the like.

The terms "halo" and "halide" refer to bromo and chloro. The term "halogen" refers to molecular bromine (Br$_2$) and molecular chlorine (Cl$_2$).

The term "a reactive halide compound" refers to free radical sources of chlorine and bromine including without limitation N-bromosuccinimide, N-chlorosuccinimide, Cl$_2$ and Br$_2$. When the reactive halide compound is Cl$_2$ or Br$_2$, the reaction preferably includes tetraalkylammonium chloride or tetraalkylammonium bromide respectively.

Methodology

The processes of this invention relate to the complete chemical synthesis of the trisaccharide glycoside αGal(1→4)βGal(1→4)Glc-OR.

Generally, these synthetic processes start with a disaccharide lactose derivative; namely, β-thiobenzyl lactoside. This compound is then differentially protected by the appropriate use of removable blocking groups, well known in the art of carbohydrate synthesis to allow further attachment of an galactose sugar unit to the acceptor structure. After attachment of the suitable blocking groups, the glycosidic linkage is formed on the anomeric carbon atom of the reducing sugar or monosaccharide. Specifically, the β-thiobenzyl group constitutes a leaving group at the anomeric center of the appropriately protected form of the lactose disaccharide structure. The donor is then reacted under catalytic conditions well known in the art with an aglycon or an appropriate form of a carbohydrate acceptor which possesses one free hydroxyl group at the position where the glycosidic linkage is to be established. A large variety of aglycon moieties are known in the art and can be attached with the proper configuration to the anomeric center of the reducing unit.

Appropriate use of compatible blocking groups, well known in the art of carbohydrate synthesis, will allow for the subsequent selective modification of the synthesized structures so as to permit further attachment of the galactose unit at the non-reducing terminus of the acceptor structure thereby resulting in formation of the αGal(1→4)βGal(1→4)Glc-OR structure.

The specifics of this synthetic protocol are described below for the preferred αGal(1→4)βGal(1→4)Glc-O(CH$_2$)$_8$COOCH$_3$ compound which is also illustrated in FIGS. 1–4. It is understood, however, that compounds other than the preferred βGal(1→4)βGal(1→4)Glc-O(CH$_2$)$_8$COOCH$_3$ compound can also be synthesized by these methods merely by the appropriate substitution of suitable reagents at the appropriate step in the synthetic process.

Specifically, as illustrated in FIG. 1, commercially available peracetylated lactoside 1 is readily converted by known methods to the corresponding β-thiobenzyl 2,2',3,3',4',6,6'-hepta-O-acetyl lactoside derivative 2 by reaction with benzylthiol (HSBn) and boron trifluoride etherate (BF$_3$.OEt$_2$). Subsequently, conventional Zemplen deacetylation (NaOMe/MeOH) yields β-thiobenzyl lactoside 3 which is preferably purified by crystallization. In this reaction, the phenyl group of the benzylthiol reagent can optionally be substituted with 1 to 2 substituents independently selected from halo, alkyl, and alkoxy.

Protecting all of the hydroxyl groups on β-thiobenzyl lactoside 3 with a removable protecting group is then achieved by first reacting β-thiobenzyl lactoside 3 with at least a stoichiometric amount of an α,α-dimethoxytoluene (DMT) in the presence of an acid catalyst to form a benzylidene group at the 4',6'-positions of the lactoside, exemplified by compound 4 in FIG. 1. Optionally, the phenyl group of DMT can be substituted with from 1 to 3 substituents independently selected from alkyl, alkoxy, cyano, halo, nitro, and trihalomethyl.

This reaction preferably employs from about 1 to about 2 equivalents of DMT per equivalent of lactoside. The reaction is conducted under anhydrous conditions to provide for a β-thiobenzyl 4',6'-di-O-benzylidene lactoside, e.g., compound 4. Preferably, the reaction is conducted at a temperature of from about 30° to about 80° C., more preferably from about 50° to about 70° C., for a period of from about 12 to about 48 hours in an inert diluent containing a catalytic amount (preferably no more than about 0.05 equivalents) of an acid catalyst such as p-toluene sulfonic acid, camphorsulfonic acid, and the like. Examples of inert diluents include tetrahydrofuran, acetonitrile, dimethylformamide, dioxane, and the like. In a particularly preferred embodiment, the reaction is conducted at between about 60° to about 70° C. for a period of about 24 hours using camphorsulfonic acid as the catalyst and tetrahydrofuran as the diluent. After reaction completion, the resulting product is recovered by conventional methods including stripping of the diluent, chromatography, crystallization and the like, or can be used directly in the next reaction procedure without purification and/or isolation.

Figure 2:
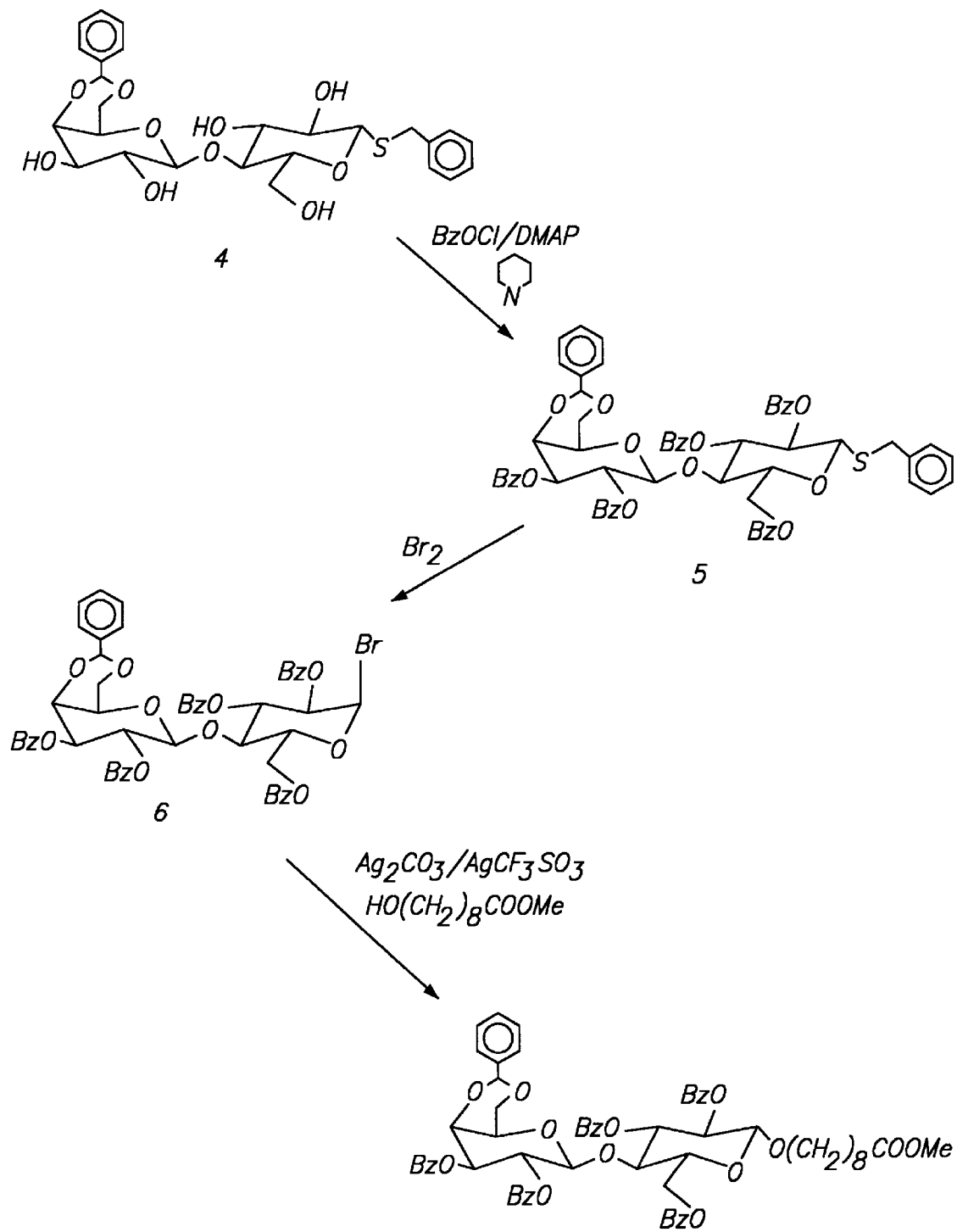

As illustrated in FIG. 2, the remaining hydroxyl groups are then protected by reaction of the β-thiobenzyl 4',6'-arylacetal lactoside, e.g., compound 4, with at least 5 equivalents, and preferably from about 5 to 15 equivalents of benzoyl chloride which is preferably added over a period of from 1 to 10 hours and more preferably ~7 hours. The reaction is conducted under anhydrous conditions to provide for the β-thiobenzyl 4',6'-benzylidene-2,2',3,3',6-penta-O-benzoyl lactoside, compound 5, wherein "Bz" represents benzoyl. Preferably, the reaction is conducted at a temperature of from about 0° to about 60° C., more preferably 15° to 30° C., in an inert diluent containing a base (e.g., pyridine) to scavenge the acid generated by the reaction. The amount of base employed is preferably at least about 5 equivalents and more preferably about 5 to 15 equivalents, based on compound 4. Additionally, in a preferred embodiment the reaction employs about 1 to 2 equivalents and more preferably about 1.0 equivalents of 4-dimethylaminopyridine (DMAP), based on compound 4.

The reaction is continued until reaction completion as evidenced by thin layer chromatography which is typically achieved after about 12 to 72 hours. Examples of suitable inert diluents include chloroform, pyridine, methylene chloride, dioxane, and the like. Upon reaction completion, the excess benzoyl chloride is destroyed by conventional means including, for example, the addition of methanol to the reaction system. The resulting product, e.g., compound 5, can then be recovered by conventional methods including stripping of the diluent, chromatography, crystallization and the like, or can be used directly in the next reaction procedure without purification and/or isolation.

Next, the β-thiobenzyl substituent of the β-thiobenzyl 4',6'-di-O-benzylidene-2,2',3,3',6-penta-O-benzoyl lactoside, compound 5, is converted to the α-bromo or the α-chloro derivative by reaction with at least a stoichiometric amount and preferably about 1 to about 5 equivalents, more preferably about 2 equivalents, of a reactive halide compound. Preferably, the reactive halide compound is employed in conjunction with from about 1 to about 5 equivalents of tetraalkylammonium halide wherein the halide is either chlorine or bromine and is preferably selected to be the same as the halide employed in conjunction with the reactive halide compound. In a preferred embodiment, the reactive halide is first added to the reaction solution and the tetraalkylammonium halide added shortly thereafter (e.g., about 3 minutes afterwards). More preferably, the reactive halide is bromine ($Br_2$) and the tetralkylammonium halide is tetraethylammonium bromide.

The reaction is conducted under anhydrous conditions to provide for α-bromo 4',6'-di-O-benzylidene-2,2',3,3',6-penta-O-benzoyl-lactoside, exemplified by compound 6. Preferably, the reaction is conducted in an inert diluent at a temperature of from about $-10°$ to about $40°$ C., and more preferably from about $0°$ to about $10°$ C. until reaction completion as evidenced by thin layer chromatography which typically occurs using reaction times ranging from about 12 to about 48 hours and preferably from about 5 to about 8 hours. Suitable inert diluents include, by way of example, chloroform, methylene chloride, dioxane, and the like. After reaction completion, excess bromide is removed by conventional means, e.g., contact with sodium thiosulfate. The resulting product can then be recovered by conventional methods including stripping of the solvent, chromatography, crystallization and the like, or can be used directly in the next reaction procedure without purification and/or isolation.

Synthesis of the aglycon substituent is achieved by reaction of the α-bromo 4',6'-di-O-benzylidene-2,2',3,3',6-penta-O-benzoyl lactoside, compound 6, with at least a stoichiometric amount and preferably an excess of a suitable hydroxy compound (i.e., HOR) in the presence of silver carbonate and a catalytic amount of silver triflate and under anhydrous conditions which provide for β-aglycon 4',6'-di-O-benzylidene-2,2',3,3',6-penta-O-benzoyl lactoside, compound 7. In a particularly preferred embodiment, the silver triflate is added as a solid to the reaction system.

Preferably, the reaction employs from about 1 to about 10 equivalents of the hydroxy compound per lactoside, e.g., compound 6, and more preferably from about 1 to about 2 equivalents. The catalytic amount of silver triflate employed preferably ranges from about 0.1 to about 1 equivalents per lactoside and the reaction is preferably conducted in an inert diluent at a temperature of from about $0°$ to about $60°$ C.

until the reaction is complete as evidenced by thin layer chromatography which typically occurs using reaction times ranging from about 2 to 12 hours and preferably from about 3 to 5 hours. Suitable inert diluents include, by way of example, chloroform, methylene chloride, and the like. The resulting product can then be recovered by conventional methods including stripping of the solvent, chromatography, crystallization and the like, or can be used directly in the next reaction procedure without purification and/or isolation.

Figure 3:
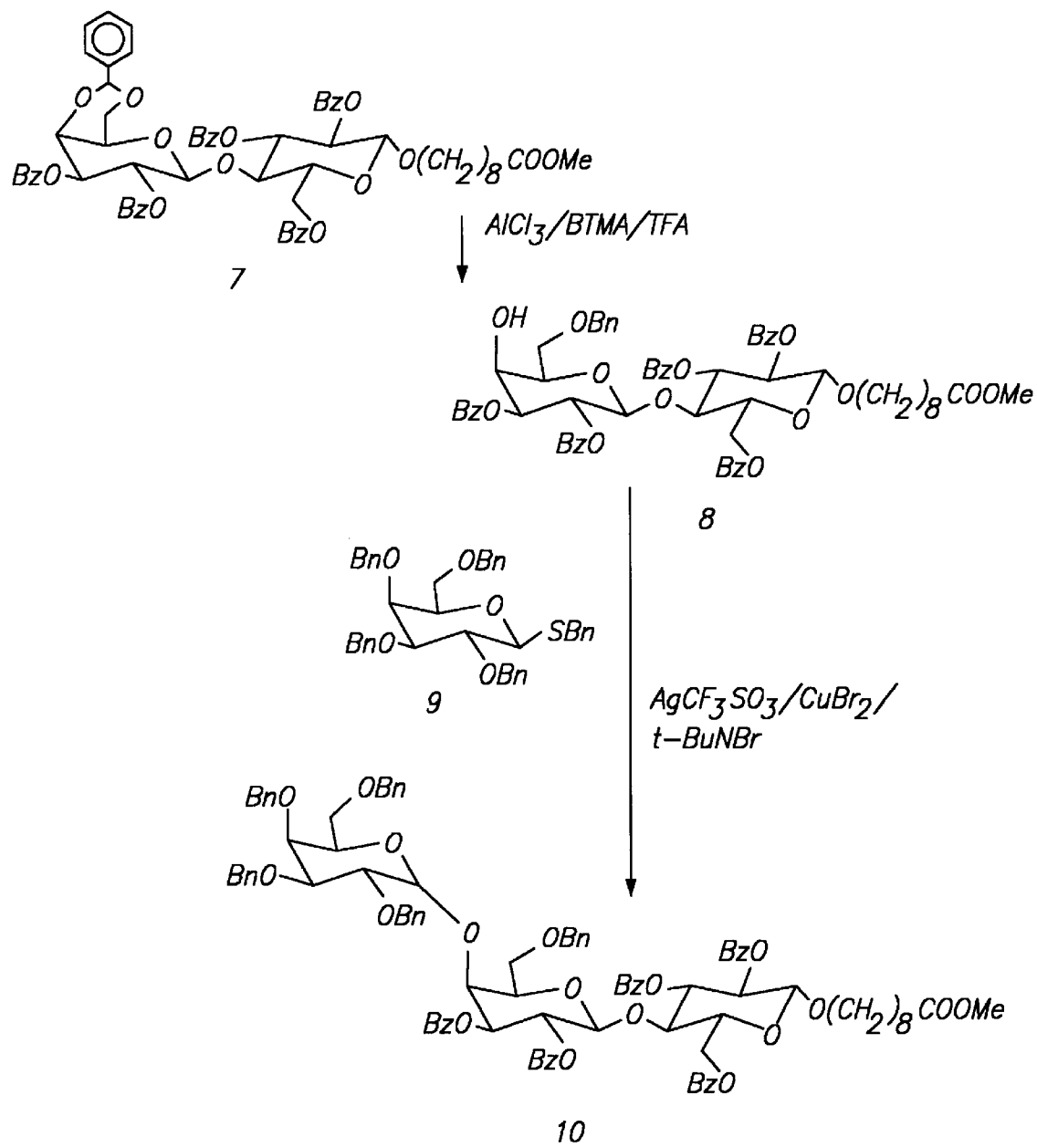

As illustrated in FIG. 3, the benzylidene substituent of β-aglycon 4',6'-di-O-benzylidene-2,2',3,3',6-penta-O-benzoyl lactoside, compound 7, is rearranged by reduction with a reducing agent such as by reaction with aluminum chloride in the presence of borane trimethylamine and trifluoro-acetic acid to provide a β-aglycon 2,2',3',3',6-penta-O-benzoyl-6'-O-benzyl-lactoside, compound 8. The reaction is preferably conducted at a temperature in the range of about $0°$ to about $20°$ C., preferably $0°$ to about $5°$ C., until the reaction is complete as evidenced by thin layer chromatography which is typically from about 2 to about 4 hours. The resulting product can then be recovered by conventional methods including stripping of the solvent, chromatography, crystallization and the like, or can be used directly in the next reaction procedure without purification and/or isolation.

Linkage of the terminal galactose group to the β-aglycon-2,2',3',3',6-penta-O-benzoyl-6'-O-benzyl-lactoside, compound 8, is accomplished by contacting the lactoside with perbenzylated thiobenzyl galactose, compound 9, in the presence of cupric bromide, silver triflate ($AgCF_3SO_3$), and tetraalkylammonium bromide under conditions which provide for a trisaccharide exemplified by compound 10. The 4' hydroxy group of the lactoside and the benzyl protecting groups of compound 9 direct the reaction to formation of the α(1→4) linkage.

Preferably, the reaction employs from about 1 to about 10 equivalents of compound 9 per equivalent of lactoside 8 and more preferably from about 1 to about 2 equivalents. Additionally, in a preferred embodiment the reaction employs from about 5 to about 7 equivalents of cupric bromide, from about 0.5 to about 1.0 equivalents of tetraalkylammonium bromide, and from about 1.5 to about 2.0 equivalents of silver triflate per equivalent of lactoside 8. The reaction is preferably conducted in an inert diluent, such as chloroform, dichloromethane, dichloroethane and the like, preferably containing about 8 to about 12 equivalents of dimethylformamide, at a temperature of from about $0°$ to about $60°$ C. until the reaction is complete as evidenced by thin layer chromatography which is typically from about 24 to about 72 hours and preferably from about 24 to about 48 hours. The resulting product can then be recovered by conventional methods including stripping of the solvent, chromatography, crystallization and the like, or can be used directly in the next reaction procedure without purification and/or isolation.

Figure 4:
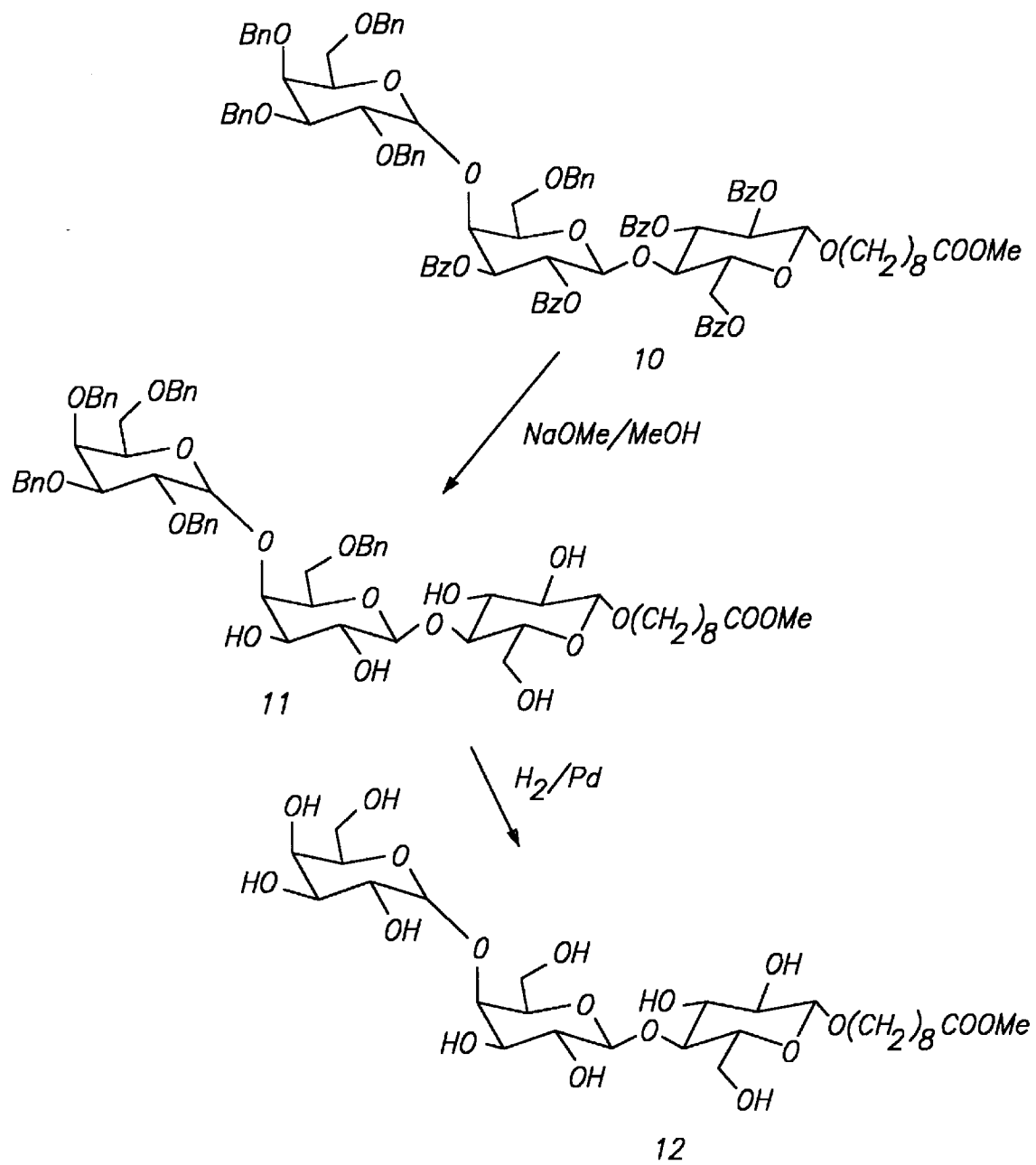

After formation of the β-aglycon trisaccharide, e.g., 10, the blocking groups are then removed by conventional methods as shown in FIG. 4 to provide for the desired αGal(1→4)βGal(1→4)Glc-OR compounds, such as 8-methoxy-carbonyloctyl α-D-galactopyranosyl-(1→4)-O-β-D-galactopyranosyl-(1→4)-O-β-D-glucopyranoside (compound 12).

As discussed above, the R aglycon preferably contains a functional group or can be derivatized to contain such a group which can provide for covalent linkage to a solid support. For example, as illustrated by Lemieux, et al.[11], and Pinto, et al.[12], the carboxymethyl (—COOCH$_3$) group of a —(CH$_2$)$_8$COOCH$_3$ aglycon can be converted under conventional conditions to the acyl azide derivative and then covalently linked to a solid support via an amide group. As discussed above, other aglycons which can be used to effect covalent linkage to a solid support can be found in Ekberg, et al.[3], Dahmen, et al.[4], Rana, et al.[5], Amvam-Zollo, et al.[6], Paulsen, et al.[7], Chernnyak, et al.[8], Fernadez-Santana, et al.[9] and Lee, et al.[10]

Utility

The methods of this invention provide for the synthesis of compounds capable of binding shiga-like toxins (SLTs) and, accordingly, are useful in the treatment of diarrhea mediated by, for example, SLTs expressed by pathogenic E. coli.[1] When so employed, the compound, either by itself or attached to a pharmaceutically acceptable solid support, can be administered as a pharmaceutical composition to a patient suffering from SLT mediated disease conditions. Oral administration of the compound coupled to a pharmaceutically acceptable solid support is preferred whereas, when the compound is not attached to a solid support, administration rectally is the preferred route.

These compounds can also be used in diagnostic assays for determining the presence of SLTs in a biological sample. For example, these compounds, appropriately labeled, can be used in a competitive assay to determine the amount and/or presence of SLTs in a compound. Suitable detectable labels include, by way of example, radiolabels, fluorescent labels, magnetic labels, enzymes, and the like. Attachment of a detectable label to these compounds is achieved via conventional methods well known in the art.

Alternatively, the trisaccharide, containing an appropriate aglycon, can be attached to a solid support in the manner described above to provide a means to remove SLTs from a sample. After contact, the solid support is freed from the biological sample by conventional means such as washing, centrifugation, etc. Additionally, such solid supports can be used in a conventional ELISA assay to detect for the presence of SLTs in a biological sample such as a stool sample.

EXAMPLES

The following examples are set forth to illustrate the claimed invention and are not to be construed as a limitation thereof.

Unless otherwise stated, all temperatures are in degrees Celsius. Also, in these examples, unless otherwise defined below, the abbreviations employed have their generally accepted meaning:

Å=Angstroms
Bn=benzyl
Bz=benzoyl
BTMA=borane trimethylamine
DCE=dichloroethane
DCM=dichloromethane
DMAP=dimethylaminopyridine
DMF=dimethylformamide
DMT=dimethoxytoluene
EDTA=ethylene diamine tetraacetic acid
equiv.=equivalents
g=gram
kg=kilogram
L=liter
M=molar
mL=milliliter
pTSA=para-toluene sulfonic acid
silver triflate=silver trifluoromethanesulfonate
TEOA=triethylorthoacetate
THF=tetrahydrofuran
TLC=thin layer chromatography Examples A–D illustrate the synthesis of the different reagents employed in the methods of this invention. Examples 1–8 provide general methods which can be used to prepare the trisaccharide glycoside αGal(1→4)βGal (1→4)Glc-OR. At the end of each examples, typical yields are provided which represent the range of actual yields achieved by repetitively conducting the synthesis per each example. In these examples, silica gel refers to 60 Å silica gel normal phase.

Example A

Synthesis of β-Thiobenzyl 2,2',3,3',4',6,6'-Hepta-O-Acetyl Lactoside (Compound 2)

The synthetic scheme employed in this example is illustrated below:

To a 20 L reaction vessel equipped with a mechanical stirrer is charged 1000 g of peracetyllactose, compound 1 (1.47 moles, 1 equivalent, available from Pfanstiehl Laboratories Inc.) and 8 L of DCE. While stirring the solution, 207 mL of benzyl mercaptan (1.76 moles, 1.2 equivalents) is added. After addition, stirring is continued for about 20 minutes until all of the peracetyllactose is dissolved. Upon dissolution, about 646 mL of redistilled boron trifluoride etherate (5.16 moles, 3.5 equivalents) is added dropwise over about 60 minutes using a 1 L addition funnel while maintaining the reaction solution at about room temperature. The reaction is then stirred at room temperature for about 30 minutes and is monitored by TLC, using 1:1 hexanes:ethyl acetate to develop the silica gel plate.

When TLC evidences reaction completion, the reaction is quenched by pouring the reaction mixture slowly into an extraction vessel containing 10 L of ice-water. The mixture is then stirred for about 15 minutes and then the organic layer is drained. The organic layer is washed with 2×10 L of cold 6% sodium bicarbonate solution. This washing step is repeated, as necessary, until pH neutrality is achieved. The organic layer is next washed with 1×10 L of water and then dried over 1000 g of anhydrous sodium sulfate while stirring for about 15 minutes. The sodium sulfate is filtered and the solids are washed with dichloromethane.

The organic layer is removed in vacuo and, to the residue, is added 6 L of hexanes and the resulting mixture is refluxed for approximately 30 minutes. After cooling, the hexanes are decanted and the remaining mixture reconcentrated to provide for the title compound.

Example B

Synthesis of β-Thiobenzyl Lactoside (Compound 3)

The synthetic scheme employed in this example is illustrated below:

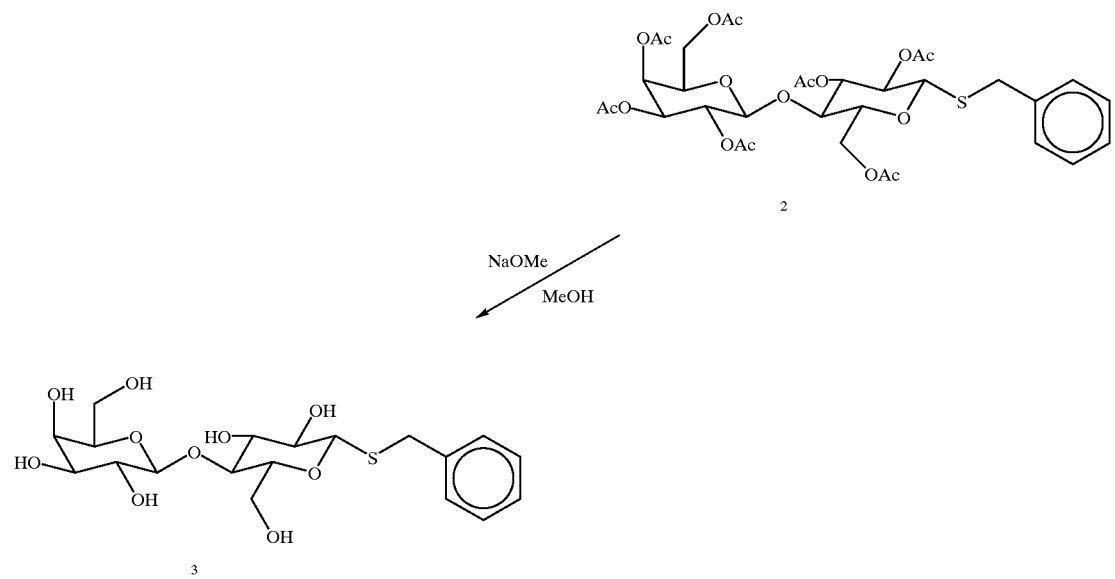

To a 20 L rotovap vessel is added about 5 L of methanol and about 1000 g of β-thiobenzyl 2,2',3,3',4',6,6'-hepta-O-acetyl lactoside (compound 2), prepared as per Example A above. The solution is then heated to about 40° C.

A pH 12 sodium methoxide/methanol solution is prepared in a separate vessel by adding about 15 g of sodium methoxide powder to about 5 L of methanol. The mixture is stirred vigorously and additional sodium methoxide is added until the solution reaches pH 12. The sodium methoxide solution is then added directed to the lactoside solution and the resulting mixture is stirred for about 12 to 24 hours. Reaction progress is monitored by silica gel TLC using 65:35:8 chloroform:methanol:water as the eluant. Upon reaction completion, the precipitated product is filtered and dried to provide for the title compound.

Example C

Synthesis of β-Thiobenzyl 2,3,4,6-Tetra-O-Benzyl Galactoside

The synthetic scheme employed in this example is illustrated below and is separated into three distinct steps labeled A, B and C as follows:

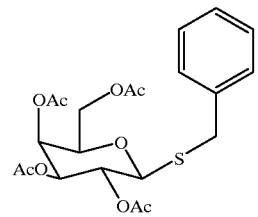

-continued

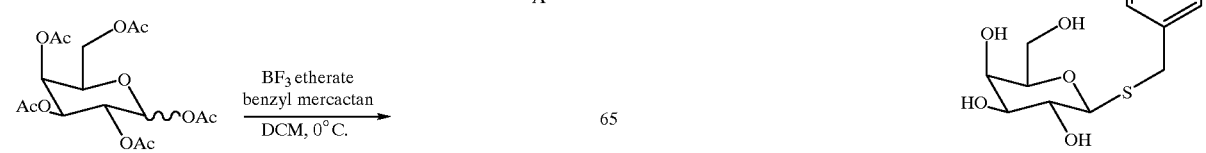

-continued

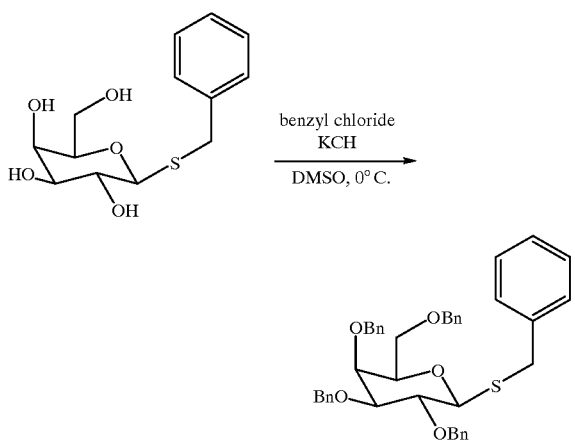

Step A

Synthesis of β-Thiobenzyl 2,3,4,6-Tetra-O-Acetyl Galactoside

To a 20 L reaction vessel, purged with nitrogen, placed in a water bath and equipped with a mechanical stirrer is charged 1000 g of peracetylgalactose (2.56 moles, 1 equivalent, available from Pfanstiehl Laboratories Inc.) and 8 L of DCM. While stirring the solution and maintaining an anhydrous nitrogen flow, 361 mL of benzyl mercaptan (3.07 moles, 1.2 equivalents) is added. After addition, stirring is continued for about 20 minutes until all of the peracetylgalactose is dissolved. Upon dissolution, about 483 mL of redistilled boron trifluoride etherate (3.84 moles, 1.5 equivalents) is added dropwise over about 60 minutes using a 0.5 L addition funnel while maintaining the reaction solution at a temperature of about 0° C. The reaction is then stirred at 0 to 5° C. for about 30 minutes and reaction progress is monitored by TLC, using 6:4 hexanes:ethyl acetate to develop the silica gel plate.

When TLC evidences reaction completion, the reaction is quenched by pouring the reaction mixture slowly into an extraction vessel containing 10 L of ice-water. The mixture is then stirred for about 15 minutes and then the organic layer is drained. The organic layer is washed with 2×10 L of cold 6% sodium bicarbonate solution. This washing step is repeated, as necessary, until pH neutrality is achieved. The organic layer is next washed with 1×10 L of water and then dried over 1000 g of anhydrous sodium sulfate while stirring for about 15 minutes. The sodium sulfate is filtered and the solids are washed with dichloromethane.

The organic layer is removed in vacuo and, to the residue, is added 6 L of hexanes and the resulting mixture is refluxed for approximately 30 minutes. After cooling, the hexanes are decanted and the remaining mixture reconcentrated to provide for β-thiobenzyl 2,3,4,6-tetra-O-acetyl galactoside.

Step B

Synthesis of β-Thiobenzyl Galactoside

To a 20 L rotovap vessel is added about 3 L of methanol and about 1000 g of β-thiobenzyl 2,3,4,6-tetra-O-acetyl galactose, prepared as per step A above. The solution is then heated to about 40° C.

A pH 12 sodium methoxide/methanol solution is prepared in a separate vessel by adding about 10 g of sodium methoxide powder to about 3 L of methanol. The mixture is stirred vigorously and additional sodium methoxide is added, as necessary, until the solution reaches pH 12. The sodium methoxide solution is then added directed to the galactoside solution and the resulting mixture is stirred for about 15 minutes. Reaction progress is monitored by silica gel TLC using 9:1 dichlormethane:methanol as the eluant.

Upon reaction completion, the solution is neutralized to pH 7 by adding methanol-washed acid resin to the mixture. The resin is then filtered off and the solution concentrated in vacuo to a syrup and, to the syrup, is added 6 L of hexanes and the resulting mixture is refluxed for approximately 30 minutes. After cooling, the hexanes are decanted and the remaining mixture reconcentrated to provide for β-thiobenzyl galactoside.

Step C

Synthesis of β-Thiobenzyl 2,3,4,6-Tetra-O-Benzyl Galactoside

To a 20 L reaction vessel, purged with nitrogen, placed in a water bath and equipped with a mechanical stirrer is added 1000 g of β-thiobenzyl galactoside (3.49 moles, 1 equivalent) prepared as per Step B above and about 8 L of DMSO. While stirring the reaction mixture, about 1293 g of potassium hydroxide (23.05 moles, 6.6 equivalents) is added and stirring is continued until the reaction mixture is homogeneous.

When homogeneity is achieved and the temperature of the reaction solution is about 0° C., 804 mL of benzyl chloride (6.98 moles, 2 equivalents) is added over a 45 minute period while maintaining the reaction solution at a temperature of about 0° C. After completion of this first aliquot of benzyl chloride, a second aliquot of 804 mL of benzyl chloride is similarly added and then a third aliquot. The total amount of benzyl chloride so added is 2412 mL (20.95 moles, 6 equivalents). The reaction is stirred continuously throughout.

One hour after addition of the final aliquot of benzyl chloride, reaction progress is monitored by silica gel TLC using 7:3 hexanes:ethyl acetate as the eluant. Upon reaction completion, the solution is diluted with 8 L of DCM and then poured slowly into 10 L of ice-water and the resulting mixture stirred for 15 minutes. Afterwards, the organic layer is drained and the aqueous layer back extracted with 5 L of DCM. The organic layers are combined and washed with 3×10 L water and then the pH is checked. The organic layer is added to 1500 g of anhydrous sodium sulfate, stirred for at least 15 minutes, filtered and then stripped to provide for a solid.

If the solid has discernible color, then the solid is added to 15 L of methanol containing about 100 g of activated charcoal. The solution is heated and then filtered hot over celite to decolorize the product. After filtering, the solvent is stripped to provide for a solid residue.

In any event, the solid is added to 15 L of methanol and the methanol heated to reflux with frequent stirring. Upon dissolution of the solids, the solution is allowed to slowly cool to room temperature whereupon the product precipitates from solution. The product is recovered by filtration and washed with cold (-10° C.) methanol and then dried to provide for the title compound.

Example D

Synthesis of 8-Methoxycarbonyloctanol

The synthetic scheme employed in this example is illustrated below:

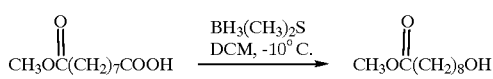

An 8 L jacketed reactor and cooling machine is assembled and the temperature of the cooling, machine is set at −10° C. The reactor is then purged with nitrogen and equipped with a mechanical stirrer. To this reactor is added 1000 g, of methyl hydrogen azelate (4.94 moles, 1 equivalent) and 4 L of DCM. The mixture is stirred while maintaining a nitrogen purge. When the reaction solution reaches about −10° C., 544 mL of borane dimethylsulfide complex (5.44 moles, 1.1 equivalents) is added dropwise to the reaction solution over about 2 hours. The reactor is vented through a moisture trap.

Upon complete addition, the temperature of the reaction solution is allowed to rise to about 15° C. and the reaction is stirred at this temperature overnight. The following day, 83 mL of ethanol is added dropwise to the reaction solution over 20 minutes and then 600 mL of water is added dropwise over 60 minutes while venting the reactor in a fume hood. After addition, the mixture is stirred for 30 minutes.

The precipitated $B(OH)_3$ is filtered and the solids washed with DCM. The filtrate is slowly added to 10 L of water and then the resulting mixture stirred for at least 15 minutes. The organic layer is drained and washed for a second time with 10 L of water, then with 1×10 L of 6% sodium bicarbonate solution and then with 2×10 L of water. The organic layer is then dried over anhydrous sodium sulfate (1000 g) and stripped to provide for the title compound.

Example 1

Synthesis of 4',6'-Di-O-benzylidene-β-thiobenzyl-lactoside (Compound 4)

The synthetic scheme employed in this example is illustrated below:

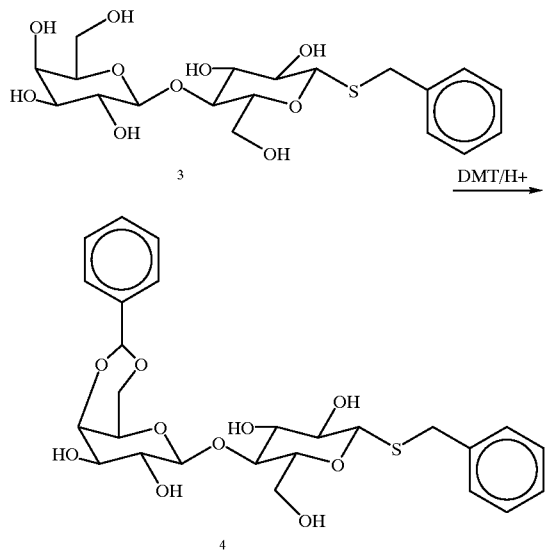

Specifically, to a 20 L reactor purged with nitrogen and equipped with a mechanical stirrer is charged 1.0 kg of thiobenzyl lactoside (2.23 mols, 1 equiv.; compound 3) and 15 L of anhydrous THF is added to make a thin suspension. To this suspension is added 502 mL α,α-dimethoxytoluene (DMT) (3.34 mols, 1.5 equiv.) and the solution stirred for about 20 minutes until homogeneous. Then 26 g of camphorsulfonic acid (0.11 mols, 0.05 equiv.) is added and the pH of the solution is between 2 and 3. The reaction mixture is brought to reflux (~65° C.) under an anhydrous atmosphere. The extent of reaction completion is monitored by TLC using 10% methanol in ethyl acetate to develop the plate. The reaction is complete after approximately 16–24 hours.

When complete, the reaction mixture is neutralized to pH 7–8 with about 10 mL triethylamine and filtered hot through a Buchner funnel. The filtrate is evaporated to a solid residue on a rotary evaporator and the solids are then redissolved in 7 L of ethyl acetate. The ethyl acetate solution is heated to reflux for approximately 90 minutes. The hot solution is then allowed to cool to room temperature and stirred there for about 16–24 hours. The resulting crystals are filtered on a Buchner funnel and washed with 1 L of 0° C. ethyl acetate. The wet crystals are then dried on the filter for 10 minutes, and then dried to yield the title compound.

Example 2

Synthesis of 4',6'-benzylidene-2,2',3,3',6-penta-O-benzoyl-β-thiobenzyl-lactoside (Compound 5)

The synthetic scheme employed in this example is illustrated below:

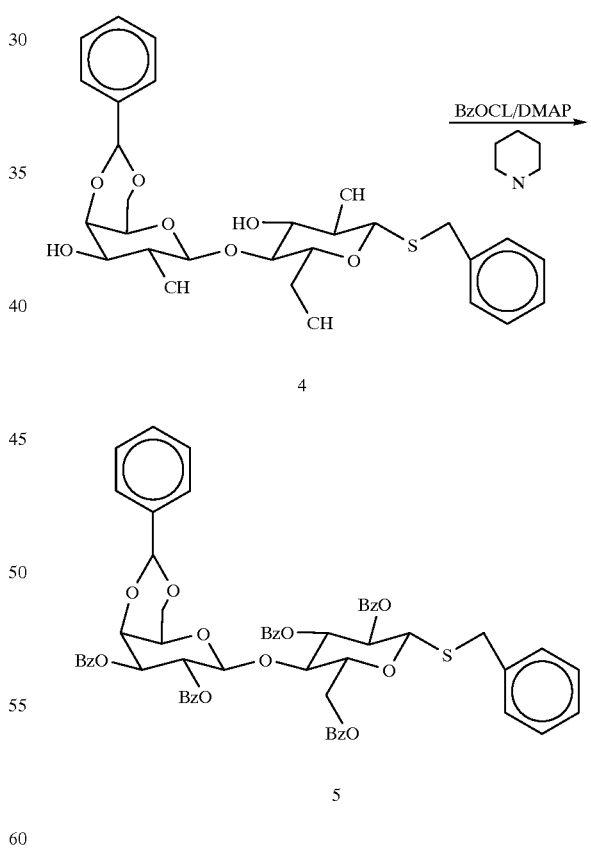

To a 20 L reaction vessel purged with nitrogen is charged 1.0 kg of β-thiobenzyl 4',6'-di-O-benzylidene-lactoside, compound 4, prepared as in Example 1 (1.86 mols, 1.0 equiv.), 1.357 L anhydrous pyridine (16.8 mols, 9.0 equiv.), 228 g of 4-DMAP (1.86 mols, 1.0 equiv.), and 10 L of anhydrous DCM. After stirring the suspension to homogeneity, 757 mL of benzoyl chloride (6.5 mols, 3.5 equiv.) is added drop-wise over 0.5 hours using an addition funnel while maintaining the temperature at about 0° C. A second aliquot of 757 mL of benzoyl chloride (6.5 mols, 3.5 equiv.) is added drop-wise again over 0.5 hours using an addition funnel while maintaining the temperature at about 0° C.

The reaction is stirred under anhydrous atmosphere for approximately 36–48 hours and is monitored by TLC, using 10% acetonitrile in DCM to develop the silica gel plate. When TLC evidences reaction completion, 0.5 L of methanol is added slowly to the rapidly stirred reaction mixture over 1 hour to consume the excess benzoyl chloride.

When the benzoyl chloride ceases reacting with methanol (i.e., the solution stops bubbling), the reaction solution is added slowly to an extraction vessel containing 10 L of ice-water. After addition, the mixture is stirred for about 15 minutes and then the organic layer is drained. The recovered organic layer is washed with 1×10 L 5% hydrochloric acid, with 1×10 L of 6% sodium bicarbonate, then with 1×10 L of water. The organic layer is repeatedly washed until neutral and then dried over 1000 g of anhydrous sodium sulfate. The sodium sulfate is then filtered and the solids are washed with dichloromethane.

The organic layer is removed in vacuo and 8 L of hexanes added to the residue and the resulting system refluxed for 30 minutes. The mixture was then cooled to room temperature, the hexanes decanted and the mixture reconcentrated to a solid. Methanol (8 L) was then added and the resulting mixture heated at reflux for approximately 4 hours. The system is allowed to cool to room temperature and stirred there for about 16 to 24 hours. The recrystallized product is filtered, the filtrate washed with methanol and subsequently dried to provide for the title compound.

The procedure set forth above was repeated several times and provides an expected yield of about 1.5–1.76 kg (80–85%) of compound 5.

Example 3

Synthesis of 4',6'-Benzylidene-2,2',3,3',6-penta-O-benzoyl-α-bromo-lactose (Compound 6)

The synthetic scheme employed in this example is illustrated below:

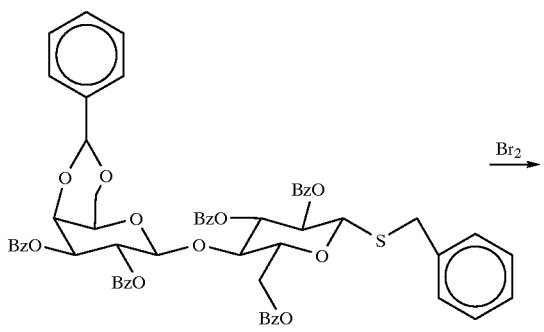

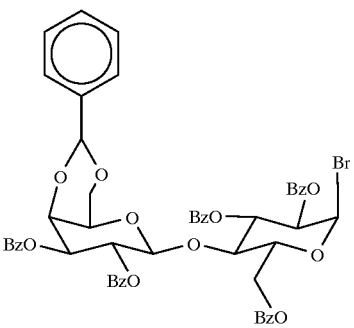

6

To a 20 L reactor purged with nitrogen, equipped with a mechanical stirrer and placed in a water bath is charged 1.00 kg β-thiobenzyl 4',6'-di-O-benzylidene-penta-O-benzoyl-lactoside, compound 5, prepared as Example 2, (0.95 mols, 1.0 equiv.) and 8 L of DCM. The mixture is stirred for about 20 minutes until dissolution is achieved.

73 mL of bromine ($Br_2$) (1.42 mols, 1.5 equiv.) is added dropwise over about 30 minutes using an addition funnel. The temperature of the reaction solution is maintained at about room temperature by addition of ice (as necessary) to the water bath. After stirring the reaction solution for about 30 minutes, 298 g tetraethylammonium bromide (1.42 mols, 1.5 equiv.) is added and the reaction is maintained at room temperature.

The reaction is stirred for approximately 5–8 hours and is monitored by silica gel TLC using 85:15:2 toluene:ethyl acetate:methanol as the eluant. The reaction is continued until completion.

When the reaction is complete, the reaction is quenched into 8 L of 7.5% sodium thiosulfate solution and stirred until there is no color to the solution. The organic layer is separated and washed with 1×10 L of 6% sodium bicarbonate solution. Washing of the organic layer is repeated until neutrality is achieved. The organic layer is then washed with 1×10 L of water, and drained into 1000 g of anhydrous sodium sulfate and the mixture stirred for at least 15 minutes. The sodium sulfate is then filtered and the solids are washed with dichloromethane.

The organic layer is removed in vacuo and the solids are dissolved in a minimum amount of dichloromethane (~1 L) then added dropwise with stirring to 10 L of methanol. The resulting mixture is stirred for 30 minutes. The crystallized product is filtered, the filtrate washed with methanol and subsequently dried to provide for the title compound.

Example 4

Synthesis of 8-Methoxycarbonyloctyl 4',6'-benzylidene-2,2',3,3',6-penta-O-benzoyl-lactoside (Compound 7)

The synthetic scheme employed in this example is illustrated below:

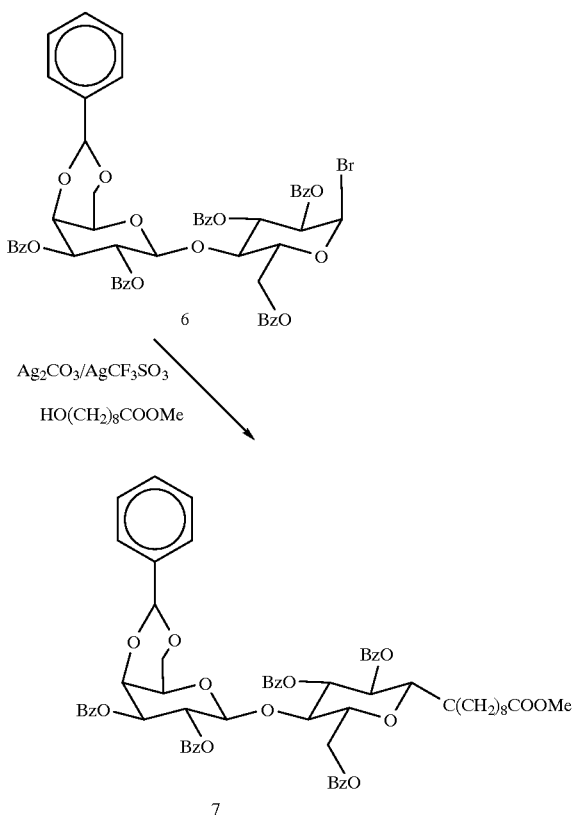

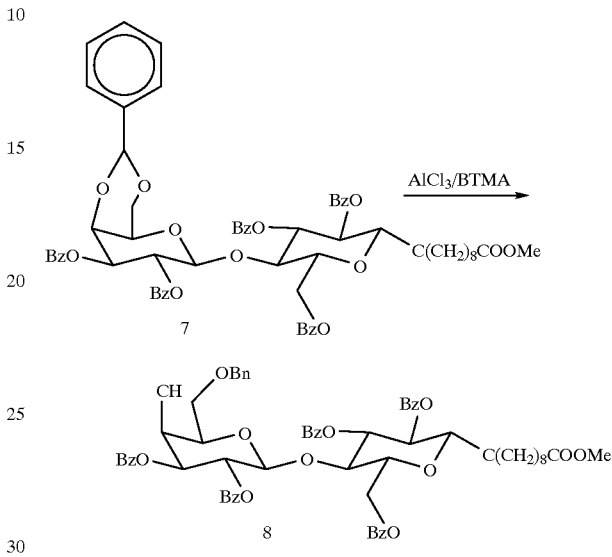

Example 5

Synthesis of 8-Methoxycarbonyloctyl 2,2',3,3',6-penta-O-benzoyl-6-O-benzyl-lactoside (Compound 8)

The synthetic scheme employed in this example is illustrated below:

To a 20 L reactor purged with nitrogen, equipped with a mechanical stirrer and wrapped with aluminum foil is charged 1.00 kg of bromo 4',6'-di-O-benzylidene-2,2',3,3',6-penta-O-benzoyl-lactoside, compound 6, prepared as in Example 3, (0.99 mols, 1.0 equiv.) and 6 L of DCM. To this reaction mixture is added 279 g 8-methoxycarbonyloctanol (1.48 mols, 1.5 equiv.) prepared as in Example D above in 1 L of DCM. The mixture is then stirred and, while stirring, 1 kg of 4A molecular sieves are added as well as 544 g of silver carbonate. The molecular sieves and silver carbonate are added by rinsing using 1 L of DCM. The mixture is stirred for 15 minutes until homogeneous.

When homogeneity is achieved, 63.3 g silver triflate (0.25 mols, 0.25 equiv.) is added. The reaction is stirred for about 0.5 hours and then monitored by silica gel TLC using 85:15:5 toluene:ethyl acetate:methanol. The reaction is continued until complete.

When the reaction is complete, the mixture is filtered through a bed of celite (~500 g), and celite bed is then rinsed with DCM. The filtrate is washed with 1×10 L of 6% NaHCO₃ solution, then with 2×10 L of water. The organic layer is dried over 1,000 g anhydrous sodium sulfate while stirring for 15 minutes. The sodium sulfate is filtered and the solids are washed with dichloromethane.

The organic layer is removed in vacuo and the solids are dissolved in a minimum amount of dichloromethane (~1 L) then added dropwise with stirring to 10 L of methanol. The resulting mixture is stirred for 30 minutes. The methanol solution is cooled to about 0° C. for about 1–2 hours and the crystallized product is filtered, the filtrate washed with methanol and subsequently dried to provide for the title compound.

To a 20 L reactor purged with nitrogen, placed in a water bath, and equipped with a mechanical stirrer is added 7 L of dry THF while maintaining an anhydrous nitrogen flow throughout this example. Aluminum trichloride, 594 g (4.46 mols, 5.0 equivalents) in approximately 100 g increments is slowly added to the reaction with stirring while maintaining the reaction mixture at about 0° C. Upon completion of the aluminum chloride addition, 325 g borane trimethylamine (BTMA) (4.46 mols., 8.0 equivalents) and 1000 g of 8-methoxycarbonyl-octyl 4',6'-di-O-benzylidene-2,2',3,3',6-penta-O-benzoyl-lactoside, compound 7, prepared as in Example 4 above, in about 1 L of dry THF is added with stirring and, upon addition, the reaction mixture is stirred for about 15 minutes.

The reaction solution is again cooled to about 0° C. and 342 mL of trifluoroacetic acid is then added dropwise over about 60 minutes while maintaining the reaction at about 0° C. The reaction is continued for about 5–8 hours (or overnight) and the reaction progress monitored by silica gel TLC using 85:15:2 toluene:ethyl acetate:methanol.

Upon reaction completion, the reaction solution is slowly poured into 10 L of ice-cold 5% sulfuric acid and stirred for about 15 minutes. The organic layer is drained and then washed with 1×10 L of ice-cold 5% sulfuric acid and then with 1×10 L of 6% aqueous sodium bicarbonate solution. The sodium bicarbonate wash is repeated as necessary until pH neutrality is reached. The organic layer is then washed with 1×10 L water, drained into 1 kg of anhydrous sodium sulfate, filtered while washing the solid sodium sulfate, and the solvent stripped to provide for a solid. The solid is dissolved in 8 L of hot methanol. The solution is cooled slowly to room temperature and then refrigerated overnight. The crystals are filtered and washed with cold (−20° C.) methanol and then dried to provide for the title compound.

Example 6

Synthesis of 8-Methoxycarbonyloctyl (2",3",4",6"-tetra-O-benzyl-α-D-galactopyranosyl)-(1→4)-O-(2',3'-di-O-benzoyl-6-O-benzyl-β-D-galactopyranosyl)-(1→4)-O-(2,3,6-tri-O-benzoyl-β-D-glucopyranoside) (Compound 10)

The synthetic scheme employed in this example is illustrated below:

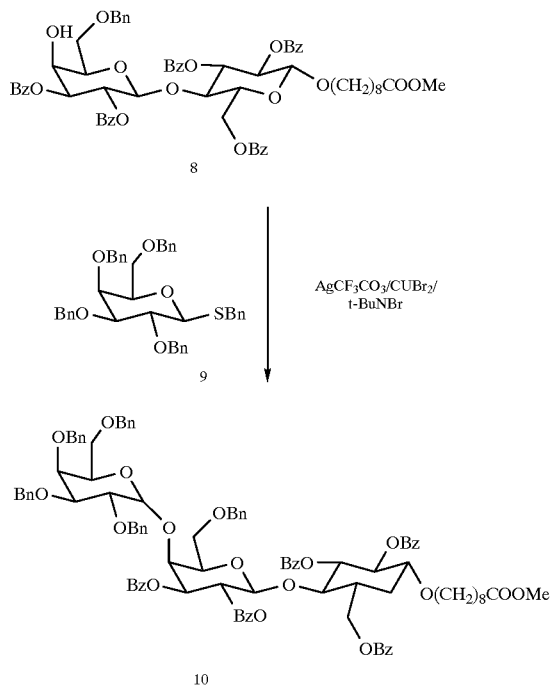

To a 20 L reactor purged with nitrogen, wrapped in aluminum foil and equipped with a mechanical stirrer, is charged 1 kg of 4A molecular sieves, 1 kg of 8-methoxycarbonyloctyl 2,2',3,3',6-penta-O-benzoyl-6-O-benzyl-lactoside, compound 8, prepared as above (0.89 moles, 1 equivalent), 994 g of copper bromide (4.45 moles, 5 equivalents), 144 g tetrabutylammonium bromide (0.45 moles, 0.5 equivalents), 864 g of β-thiobenzyl 2,3,4,6-tetra-O-benzyl-galactoside (1.34 moles, 1.5 equivalents) and 689 mL of anhydrous DMF (8.9 moles, 10 equivalents). Subsequently, 7.94 L of anhydrous DCE and 1.62 L anhydrous toluene (5:1 ratio of DCE:toluene) are added and the reaction mixture is stirred for about 40 minutes. Then 343 g of silver triflate (1.34 moles, 1.5 equivalents) is added in 50 g portions over a period of 3.5 hours (one addition every 30 minutes) and the reaction mixture is stirred for 24–48 hours. The reaction progress is monitored by silica gel TLC using 85:15 toluene:ethyl acetate as the eluant. If the reaction is not complete after 48 hours, an additional 148 g tetrabenzyl thiogalactoside (0.23 moles, 0.25 equivalents) can be added and the resulting reaction mixture is stirred an additional 16 hours.

When the reaction is complete by TLC, the mixture is filtered through a celite pad which is rinsed with DCM. The filtrate is then washed with 2×10 L of saturated EDTA solution, with 1×10 L of an aqueous 6% sodium bicarbonate solution and then with 2×10 L of water. The organic layer is then dried over 1000 g anhydrous sodium sulfate while stirring for at least 15 minutes, filtered while washing the solids with DCM and the filtrate is concentrated in vacuo to a solid.

This solid is purified on a silica gel column (i.e., 5 inch stainless steel column containing about 9 kg of LiChroprep™ silica gel (available from EM Science) which equilibrated with 98:2 dichloromethane:acetonitrile. The column is eluted with the same solvent mixture and the appropriate fractions collected. The pooled fractions are then concentrated in vacuo to provide the title compound, i.e., compound 10.

Example 7

Synthesis of 8-methoxycarbonyloctyl (2",3",4",6"-tetra-O-benzyl-α-D-galactopyranosyl)-(1→4)-O-(6-O-benzyl-β-D-galactopyranosyl)-(1→4)-O-β-D-glucopyranoside (Compound 11)

The synthetic scheme employed in this example is illustrated below:

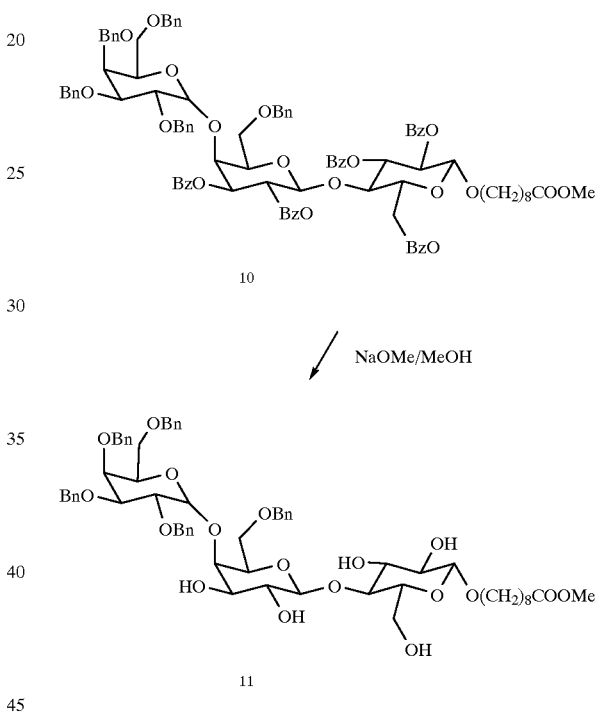

To a 20 L reactor purged with nitrogen and placed into a 30° C.–40° C. jacketed reactor is added about 13 L of anhydrous methanol and about 1000 g of 8-methoxycarbonyloctyl (2",3",4",6"-tetra-O-benzyl-α-D-galactopyranosyl)-(1→4)-O-(2',3'-di-O-benzoyl-6-O-benzyl-β-D-galactopyranosyl)-(1→4)-O-(2,3,6-tri-O-benzoyl-β-D-glucopyranoside), compound 10 while maintaining a nitrogen purge throughout.

A 0.5 N sodium methoxide solution is prepared in a separate vessel by adding about 12 g of metallic sodium to about 1.1 L of anhydrous methanol. The mixture is stirred vigorously until all of the metal dissolves. A sufficient amount of the resulting sodium methoxide solution is then added directly to the trisaccharide solution until the combined solution has a pH of about 12. The reactor is purged with nitrogen and the resulting mixture is stirred for overnight at about 30° C.–40° C. Reaction progress is then monitored by silica gel TLC using 98:2 dichlormethane:methanol as the eluant.

Upon reaction completion, the solution is neutralized to pH 7 by adding methanol-washed and vacuum dried IR 120 acid resin to the mixture. The resin is then filtered off and the solution concentrated in vacuo to a syrup and, to the syrup, is added 8 L of hexanes and the resulting mixture is refluxed for approximately 30 minutes. After cooling, the hexanes are decanted. The remaining mixture is reconcentrated to provide for a syrup containing the title compound. The resulting syrup is then dissolved in 8 L of ethyl acetate and water washed with 10 L of water. The organic layer is concentrated to a syrup once more. The syrup is dissolved in 2 L of methanol and 0.2μ filtered to remove remaining traces of solid particles. The filtrate is once again concentrated to a syrup and dried under high vacuum for 12 hours to provide for the title compound.

Example 8

Synthesis of 8-methoxycarbonyloctyl α-D-galactopyranosyl-(1→3)-O-β-D-galactopyranosyl-(1→4)-O-β-D-glucopyranoside (Compound 12)

The synthetic scheme employed in this example is illustrated below:

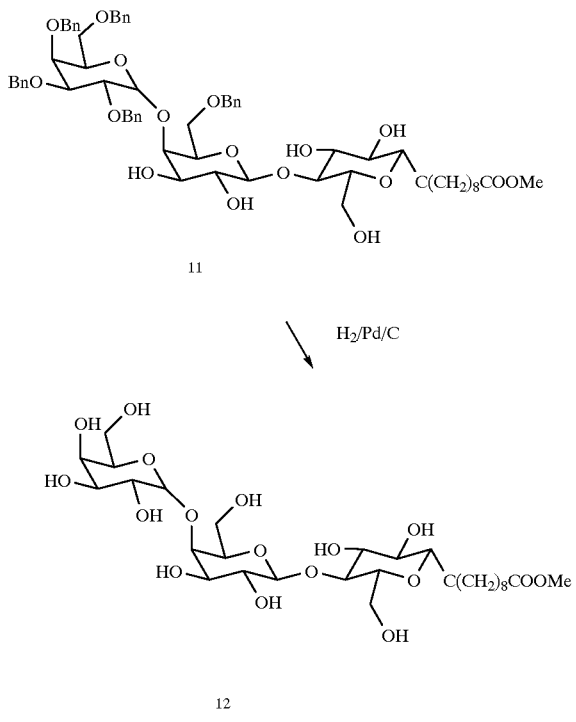

To a rotovap vessel is added 1 kg of compound 11, prepared as in Example 7 above (0.798 mols, 1.00 equiv.) and 11 L of glass distilled methanol. The solution is heated to about 40° C. in a rotovap. After complete dissolution, the vessel is removed from the rotovap and the solution transferred to a 20 L reactor using about 1 L of methanol to effect transfer. The reactor is then purged with nitrogen for 15 minutes and then 339 g of 5% palladium on charcoal added. After addition, the mixture is stirred and purged with nitrogen for 15 minutes. The nitrogen flow is then stopped and hydrogen ($H_2$) introduced into the sealed reactor which is vented into a mercury bubbler. After 5–8 hours of stirring, reaction progress is monitored by silica gel TLC using 65:35:8 chloroform:methanol:water as the eluant.

After reaction completion, the reaction mixture is filtered through a Celite, (trademark) filter aid, bed (~500 g of Celite) and the bed is then thoroughly washed with methanol. The filtrate is concentrated in vacuo to a solid and the solid dissolved in 5.6 L of methanol. The methanol solution is heated over a steam bath and then 11.2 L of ethyl acetate is slowly added while ensuring that the product remains totally in solution.

The resulting solution is allowed to cool slowly to room temperature and then refrigerated overnight to crystallize the product. The crystals are recovered and rinsed with cold (−10° C.) ethyl acetate and then dried to provide for the title compound.

Although the foregoing invention has been described in some detail by way of illustration and example for purposes of clarity and understanding, it will be apparent that certain changes and modifications may be practiced within the scope of the appended claims.

What is claimed is:

1. A process for the synthesis of αGal(1→4)βGal(1→4)Glc-OR$^1$ compounds which process comprises:
    (a) contacting β-thio-R lactoside with at least a stoichiometric amount of an α,α-dialkoxytoluene wherein the toluene group is optionally substituted on the phenyl ring with 1 to 3 substituents independently selected from alkyl, alkoxy, cyano, halo, nitro, and trihalomethyl under conditions to provide for β-thio-R 4'-6'-di-O-benzylidine lactoside
    wherein R is selected from the group consisting of alkaryl, alkyl and aryl optionally substituted with 1 to 2 substituents selected from halo, alkyl, and alkoxy and farther wherein the benzylidene group of the resulting β-thio-R 4'-6'-di-O-benzylidene lactoside is optionally substituted on the phenyl ring with 1 to 3 substituents selected from alkyl, alkoxy, cyano, halo, nitro, and trihalomethyl;
    (b) benzoylating the compound produced in (a) above with at least 5 equivalents of benzoyl halide under conditions to provide for β-thio-R 4',6'-di-O-benzylidene-2,2',3,3',6-penta-O-benzoyl-lactoside;
    (c) contacting the compound produced in (b) above with a reactive halide compound under conditions to provide for either the α-chloro 4',6'-di-O-benzylidene-2,2',3,3',6-penta-O-benzoyl-lactoside or the α-bromo 4',6'-di-O-benzylidene-2,2',3,3',6-penta-O-benzoyl-lactoside;;
    (d) contacting the compound produced in (c) above with a compound of the formula HOR$^1$ where R$^1$ is an aglycon of at least one carbon atom under conditions to provide for β-aglycon 4',6'-di-O-benzylidine-2,2',3,3',6-penta-O-benzoyl-lactoside;
    (e) contacting the compound produced in (d) above with a reducing agent under conditions which provide for β-aglycon 2,2',3,3',6-penta-O-benzoyl-6'-O-benzyl-lactoside wherein the benzyl group is optionally substituted on the phenyl ring with 1 to 3 substituents selected from alkyl, alkoxy, cyano, halo, nitro, and trihalomethyl;
    (f) contacting the compound produced in (e) above with β-thiobenzyl 2,3,4,6-tetra-O-benzyl-D-galactose under conditions to provide for aglycon (2",3",4",6"-tetra-O-benzyl-α-D-galactopyranosyl)-(1→4)-O-(2',3'-di-O-benzoyl-6'-O-benzyl-β-D-galactopyranosyl)-(1→4)-O-(2,3,6-tri-O-benzoyl-β-D-glucopyranoside); and
    (g) removing the benzyl and benzoyl protecting groups in the compound produced in (f) above under conditions to provide for α-D-galactopyranosyl-(1→4)-O-β-D-galactopyranosyl-(1→4)-O-β-D-glucopyranoside which can also be referred to as αGal(1→4)βGal(1→4)Glc-OR$^1$ where R$^1$ is an aglycon of at least 1 carbon atom.

2. The method according to claim 1 wherein R is an alkaryl group.

3. The method according to claim 2 wherein R is benzyl.

4. The method according to claim 1 wherein the reactive halide compound is $X_2$ wherein X is bromo or chloro.

5. The method according to claim 4 wherein the reactive halide compound is used in combination with tetraalkylammonium halide.

6. The method according to claim 1 wherein the aglycon contains from 1 to 20 carbon atom.

7. The method according to claim 1 wherein the aglycon contains from 1 to 10 carbon atoms.

8. The method according to claim 1 wherein said β-thio-R lactoside is prepared by:

(a) contacting at least a stoichiometric amount of RSH with peracetyl lactose wherein R is selected from the group consisting of alkyl, aryl, alkaryl and aryl substituted with 1 to 3 substituents selected from halo, alkyl and alkoxy under conditions which form the β-thio-R 2,2',3,3',4,6,6'-hepta-O-acetyllactoside; and (b) deacetylating the product produced in (a) above under conditions to provide for β-thio-R lactoside.

9. A method for the synthesis of αGal(1→4)βGal(1→4)Glc-O(CH$_2$)$_8$COOCH$_3$ which comprises:

(a) contacting β-thiobenzyl lactoside with at least a stoichiometric amount of a α,α-dimethoxytoluene under conditions to form β-thiobenzyl 4'-6'-di-O-benzylidene lactoside;

(b) benzoylating the compound produced in (a) above with at least 5 equivalents of benzoyl halide under conditions to provide for β-thiobenzyl 4',6'-di-O-benzylidene-2,2',3,3',6-penta-O-benzoyl-lactoside;

(c) contacting the compound produced in (b) above with $X_2$ wherein X is selected from the group consisting of Br and Cl under conditions to provide for either the α-bromo 4',6'-di-O-benzylidene-2,2',3,3',6-penta-O-benzoyl-lactoside or the α-chloro 4',6'-di-O-benzylidene-2,2',3,3',6-penta-O-benzoyl-lactoside;

(d) contacting the compound produced in (c) above with a compound of the formula HO(CH$_2$)$_8$COOCH$_3$ under conditions to provide for 8-methoxycarbonyloctyl 4',6'-di-O-benzylidene-2,2',3,3',6-penta-O-benzoyl lactoside;

(e) treating the compound produced in (d) above with a reducing agent under conditions to provide for 8-methoxycarbonyloctyl 2,2',3,3',6-penta-O-benzoyl-6'-O-benzyl-lactoside;

(f) contacting the compound produced in (e) above with β-thiobenzyl 2,3,4,6-tetra-O-benzyl-D-galactose to provide for 8-methoxycarbonyloctyl (2",3",4",6"-tetra-O-benzyl-α-D-galactopyranosyl)-(1→4)-O-(2',3'-di-O-benzoyl-6'-O-benzyl-β-D-galactopyranosyl)-(1→4)-O-(2,3,6-tri-O-benzoyl-β-D-glucopyranoside); and (g) removing each of the benzyl and benzoyl protecting groups in the compound produced in (f) above under conditions to provide for 8-methoxycarbonyloctyl-α-D-galactopyranosyl-(1→4)-O-β-D-galactopyranosyl-(1→4)-O-β-D-glucopyranoside which can also be referred to as αGal(1→4)βGal(1→4)Glc-O(CH$_2$)$_8$COOCH$_3$.

10. The method according to claim 8 wherein, after addition of $X_2$, at least a stoichiometric amount of tetraalkylammonium halide is added to the reaction mixture.

* * * * *